United States Patent
Evans (10) Patent No.: US 10,682,475 B2
(45) Date of Patent: Jun. 16, 2020

(54) NEEDLE TIP STORAGE AND REMOVAL DEVICE

(71) Applicant: OWEN MUMFORD LIMITED, Brook Hill, Woodstock, Oxford, Oxfordshire (GB)

(72) Inventor: Timothy Evans, Oxfordshire (GB)

(73) Assignee: Owen Mumford Limited, Oxford (GB)

(*) Notice: Subject to any disclaimer, the term of this patent is extended or adjusted under 35 U.S.C. 154(b) by 262 days.

(21) Appl. No.: 14/365,788

(22) PCT Filed: Dec. 17, 2012

(86) PCT No.: PCT/GB2012/053164
§ 371 (c)(1),
(2) Date: Jun. 16, 2014

(87) PCT Pub. No.: WO2013/088178
PCT Pub. Date: Jun. 20, 2013

(65) Prior Publication Data
US 2015/0119818 A1    Apr. 30, 2015

Related U.S. Application Data

(60) Provisional application No. 61/576,506, filed on Dec. 16, 2011.

(30) Foreign Application Priority Data

Dec. 16, 2011 (GB) ..................................... 112166.8

(51) Int. Cl.
*A61M 5/32* (2006.01)
*A61M 5/00* (2006.01)

(52) U.S. Cl.
CPC .......... *A61M 5/3298* (2013.01); *A61M 5/002* (2013.01); *A61M 5/3204* (2013.01); *A61M 5/3213* (2013.01); *A61M 2005/3208* (2013.01)

(58) Field of Classification Search
CPC .... A61M 5/50; A61M 5/3202; A61M 5/3204; A61M 5/3205; A61M 5/3213
(Continued)

(56) References Cited

U.S. PATENT DOCUMENTS 4,248,246 A    2/1981   Ikeda
4,778,453 A    10/1988  Lopez
(Continued)

FOREIGN PATENT DOCUMENTS

EP    0225951 A1   6/1987
EP    0990446 A1   4/2000
(Continued)

OTHER PUBLICATIONS

Autopen 24; Owen Mumford, "Autopen 23 is an easy to use insulin injection pen, designed for use with 3.0ml sanofi aventis insulin cartridges. Compatible with all pen needles", last reviewed Apr. 2006.
(Continued)

*Primary Examiner* — Allan D Stevens
(74) *Attorney, Agent, or Firm* — Quarles & Brady LLP (57) ABSTRACT

Various needle tip storage and removal devices are disclosed which include a housing with a separate storage compartment and removal compartment for receiving a needle tip. The removal compartment is designed to hold securely a used needle tip. The removal compartment may have a one way snap engagement and/or a movable closure element.

5 Claims, 13 Drawing Sheets

(58) Field of Classification Search
USPC .................................... 604/110, 192, 263
See application file for complete search history.

(56) References Cited

U.S. PATENT DOCUMENTS

| | | | |
|---|---|---|---|
| 4,883,470 A | 11/1989 | Haindl | |
| 4,919,264 A | 4/1990 | Shinall | |
| 4,973,315 A | 11/1990 | Sincock | |
| 4,984,689 A * | 1/1991 | Emalfarb | A01G 9/28 206/499 |
| 5,026,345 A | 6/1991 | Teringo | |
| 5,084,027 A * | 1/1992 | Bernard | A61M 5/3213 206/365 |
| 5,347,078 A * | 9/1994 | Eckels | A61M 5/3213 206/365 |
| 5,554,129 A | 9/1996 | Stevenson | |
| 5,718,689 A * | 2/1998 | Stevenson | A61M 5/3213 128/919 |
| 5,968,021 A | 10/1999 | Ejlersen | |
| 6,315,113 B1 | 11/2001 | Britton et al. | |
| 6,923,318 B1 | 8/2005 | Erickson et al. | |
| 7,021,463 B2 | 4/2006 | Phan | |
| 7,063,683 B2 * | 6/2006 | Teringo | A61M 5/3213 604/110 |
| 2003/0015444 A1 | 1/2003 | Molin et al. | |
| 2004/0034318 A1 | 2/2004 | Fritz et al. | |
| 2005/0016883 A1 | 1/2005 | Phan | |
| 2006/0032769 A1 | 2/2006 | Erickson et al. | |
| 2006/0243619 A1 | 11/2006 | Brown et al. | |
| 2008/0308441 A1 | 12/2008 | Erickson et al. | |
| 2009/0236347 A1 | 9/2009 | Erickson et al. | |
| 2010/0063457 A1 | 3/2010 | Crossman | |
| 2010/0122925 A1 | 5/2010 | Charbonneau | |
| 2011/0071475 A1 | 3/2011 | Horvath et al. | |

FOREIGN PATENT DOCUMENTS

| | | |
|---|---|---|
| EP | 1669097 A2 | 6/2006 |
| EP | 1741459 A1 | 1/2007 |
| EP | 2257236 A1 | 12/2010 |
| EP | 2298224 A1 | 3/2011 |
| EP | 2298397 A1 | 3/2011 |
| GB | 2437923 A | 11/2007 |
| JP | 2000140104 A | 5/2000 |
| JP | 2000-262616 A | 9/2000 |
| JP | 2009-536539 A | 10/2009 |
| JP | 2011-062527 A | 3/2011 |
| WO | 97/40869 A1 | 11/1997 |
| WO | 03080467 A1 | 10/2003 |
| WO | 2005/011781 A1 | 2/2005 |
| WO | 2007006164 A1 | 1/2007 |
| WO | 2009/117505 A1 | 9/2009 |
| WO | 2010/042680 A1 | 4/2010 |
| WO | 2011/018408 A1 | 2/2011 |

OTHER PUBLICATIONS

Autopen—Insulin Delivery Pens, Owen Mumford, http://www.owenmumford.com/en/range/6/autopen.html, 2013.
AutoPen 24 for use with Glargine 3ml cartriges, Salisbury Health Care, NHS Trust, pp. 1, Jan. 1, 2005.
Pentips instructions, Choosing an injection site, Choosing a pen needle.
Unifine Pentips, Pen Needles, Owen Mumford, http://www.owenmumford.com/en/range/7/unifine-pentips.html, Jul. 29, 2012.
Office Action issued in Chinese Patent Application No. 201280062216.X, dated Mar. 23, 2016, 3 pages.
GB Search Report, dated Mar. 21, 2012, from correspond GB application.
GB Search Report, dated Aug. 9, 2012, from correspond GB application.
International Search Report, dated May 31, 2013, from corresponding PCT application.
English translation of Office Action issued in counterpart Japanese Patent Application No. 2014-546653, dated May 4, 2016, 5 pages.
Examination Report; United Kingdom Application No. GB1121667.8, dated Nov. 20, 2017, 8 pages.
English Translation of Office Action issued in corresponding Japanese Patent Application No. 2014-546653, dated May 9, 2017, 5 pages.
First Office Action issued in corresponding Chinese Patent Application No. 201610663311.5, dated Dec. 20, 2018, 15 pages.

* cited by examiner

NEEDLE TIP STORAGE AND REMOVAL DEVICE

This invention relates to a needle tip storage and removal device and in particular, but not exclusively, to such a device for use with a pen injector apparatus or the like intended to inject a number of metered doses from a cartridge of therapeutic material.

In a conventional automatic injector such as the Owen Mumford Autopen®, a cartridge of therapeutic material is loaded into a cartridge holder and a single use needle tip is screwed onto the forward end of the device. A typical example of a needle tip (otherwise known as a pen needle) is our Unifine® pen needle. The needle tip has a double-ended needle, the rear end of which penetrates a rubber membrane in the forward end of the cartridge as the needle tip is screwed on. A metered dose can then be dialled into the automatic injector, the forward end of the needle pushed into the injection site, and a trigger on the device actuated to inject the metered dose. After the injection, the needle tip should be removed from the device and discarded.

In many conventional arrangements, the cylindrical exterior of the needle tip hub is provided with splines or flutes and the needle tip is supplied in a foil-sealed container, having a complementary splined cylindrical socket. To use such a needle tip, the foil is removed and the needle tip, with the needle still shrouded by the container, is screwed onto the injection device using the container as a spanner or wrench. Once fully home, the container may be withdrawn axially leaving the needle exposed, although in some instances a removable secondary needle shield is provided. Following injection, the user may slide the container back onto the needle hub and use it again as a spanner or wrench to remove the needle tip. The needle tip can then be safely discarded because the used needle is now received in the container. This system works extremely well provided the user retains the container and uses it to remove the needle tip immediately after the injection. However, in many instances, users may not follow the recommendation to change the needle tip after each injection and may instead use the same needle tip for several injections over an extended period. In this case they may have discarded the original container and so may be left to remove the needle tip by unscrewing by hand it whilst the needle is still exposed. This provides a risk of needle stick injury both whilst removing the needle tip and when it is discarded.

Accordingly, in one aspect this invention provides a needle tip storage and removal device comprising a storage compartment for receiving in use an unused needle tip of a given drive configuration comprising a cylindrical skirt, and, adjacent the storage compartment, a removal compartment for receiving in use a used needle tip of said given configuration, wherein the removal compartment includes a movable closure element associated with the device which is movable between an open position in which the removal compartment is accessible and a closed position in which the closure element closes the compartment preventing access to the compartment and any needle tip contained therein.

Preferably the storage compartment and the removal compartment are each adapted to receive a single pen tip only. Preferably each of the storage and removal compartments includes a respective socket configured to slidably and non-rotatably receive a needle tip.

In one embodiment the closure element comprises a cap hinged to the device and hingeable between said open and closed positions. Here the cap and said hinge are conveniently integrally moulded with said removal compartment. Advantageously said cap includes a feature that cooperates with a corresponding feature adjacent the socket to provide a snap engagement when the cap is closed.

In another embodiment said closure element is slideable between said open and closed positions. The closure element may for example include a flexible member slideably mounted in a housing of said device and having an externally accessible pad for manual engagement to move said closure element between its open and closed positions. Conveniently the flexible member is constrained to slide in a track formed in said device. The track may conveniently comprise two angled portions, whereby the manual sliding action is linear and in a direction generally perpendicular to the direction of movement of the leading edge of the flexible member when moving towards its closed position.

Alternatively said closure element may comprise a shutter mounted on the exterior of the device and movable between open and closed positions. For example the shutter may include spaced claw members adapted to slide in corresponding tracks in an outer housing.

Conveniently the device includes a latch arrangement to latch the closure element in its closed position relative to the removal compartment.

According to another aspect, this invention provides a needle tip storage and removal device comprising a storage compartment for receiving in use an unused needle tip of a given drive configuration comprising a cylindrical skirt, and, adjacent the storage compartment, a removal compartment for receiving in use a used needle tip of said given configuration, wherein the removal compartment includes a removal socket and snap engagement means adjacent the outer periphery of the socket for cooperating with said skirt to retain a used needle tip when pressed into said removal socket in use.

The snap engagement means may comprise spaced arcuate rib portions directed radially inwardly around the periphery of the removal socket. Thus the removal compartment may be formed of moulded plastics material, and the snap engagement means may be formed of a different plastics material, in an over-moulding process.

Conveniently, the removal socket is designed so that in use a used needle tip may be fully retained in said socket by said snap engagement means, without protruding beyond the socket.

In one embodiment the storage container includes wall regions extending away from the socket to define a dished profile, when viewed in a direction transverse to a direction, into which a used needle tip may be inserted into the removal compartment in use.

In another embodiment a peripheral flange extends around at least part of the periphery of the removal socket and has a textured surface, for example roughened, toothed or jagged.

Preferably each of the storage and removal compartments comprises walls defining a generally cylindrical socket for the hub of the needle tip and, extending away therefrom, an elongate narrower passage to receive the needle of the needle tip, with the storage compartment and the removal compartment being oppositely directed.

In one arrangement the forward end of the passage in a given compartment lies alongside the cylindrical socket of the other, with the passages staggered longitudinally.

Alternatively, the passages may lie generally parallel and alongside each other and project towards the socket of the other compartment thereby to reduce the transverse cross section of the device, and make its disposal into the restricted cross section aperture of a sharps bin easier.

According to another aspect, this invention provides a needle tip storage and removal device comprising a storage compartment for receiving in use an unused needle tip of a given drive configuration comprising a cylindrical skirt, and, adjacent the storage compartment, a removal compartment for receiving in use a used needle tip of said given configuration, wherein each of the storage and removal compartments comprises walls defining a generally cylindrical socket for the hub of the needle tip, and extending away therefrom an elongate narrower passage to receive the needle of the needle tip, with the storage compartment and the removal compartment being oppositely directed, and wherein the respective passages lie generally parallel and alongside each other and project towards the socket of the other compartment, and preferably inversely aligned such that the leading end of the passage is level with the trailing end of the other passage and vice versa.

The storage and removal compartments preferably receive the needle tip non-rotationally so that the device can be used as a spanner to screw and unscrew the needle tip from the medicament container.

The invention also extends to a needle tip storage and removal device as described in any of the aspects above, with an unused needle tip located within the storage compartment and sealed therein by a removable closure of foil or the like.

By way of example only, various specific embodiments of the invention will be described in detail, reference being made to the accompanying drawings in which.

The needle tip storage and removal devices as to be described below are intended for use with a needle tip 10 of the type shown in FIG. 1. The needle tip 10 comprises a generally cylindrical, splined needle hub 12 from the forward end of which extends a needle and which is threaded internally. The needle 14 is double ended and protrudes part way into the internally threaded cylindrical recess defined by the cylindrical skirt of the hub.

Referring generally to each of the described embodiments, these comprise a storage compartment 16 and a removal compartment 18. Each compartment is of similar form and comprises a socket portion designed to receive the needle hub and, communicating therewith, an elongate passage designed to accommodate the needle and any sheath provided therewith. Both the storage and removal compartments carry internal splines so that the needle tip may be slid into and out of the container but does not rotate in the compartment.

In a device as supplied, a sterile, unused needle tip 10 is housed in the storage compartment 16 and sealed by a foil seal (not shown), and the removal compartment 18 is empty. In use, assuming that the pen injector or the like has a used needle tip 10 on it, the needle tip storage and removal device is offered up to the needle tip so that the needle tip 10 slides into the removal compartment 18 in non-rotatable engagement, so that the pen injector can be unscrewed from the used needle tip. The used needle tip 10 is retained in the removal compartment 18 and the user then removes the foil seal or the like from the storage compartment 16 to reveal the sterile, unused needle tip. The user can then offer the pen injector up to the needle tip and screw it on. The embodiments below provide various safety features designed to improve the technical performance of the device; these features may be modified or combined.

Figure 2A:
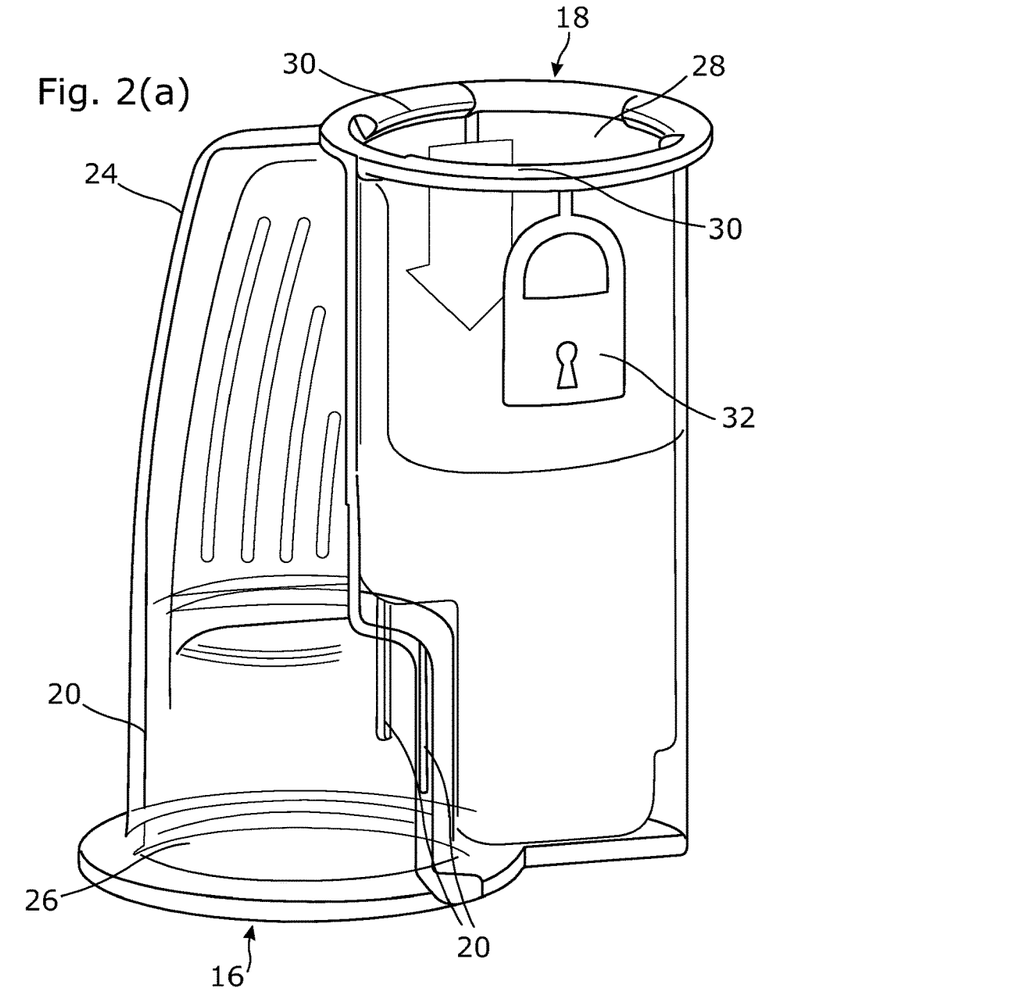
FIGS. 2(a) and (b) are side and detail views respectively on a first embodiment of needle tip storage and removal device in accordance with this invention.
Figure 2B:
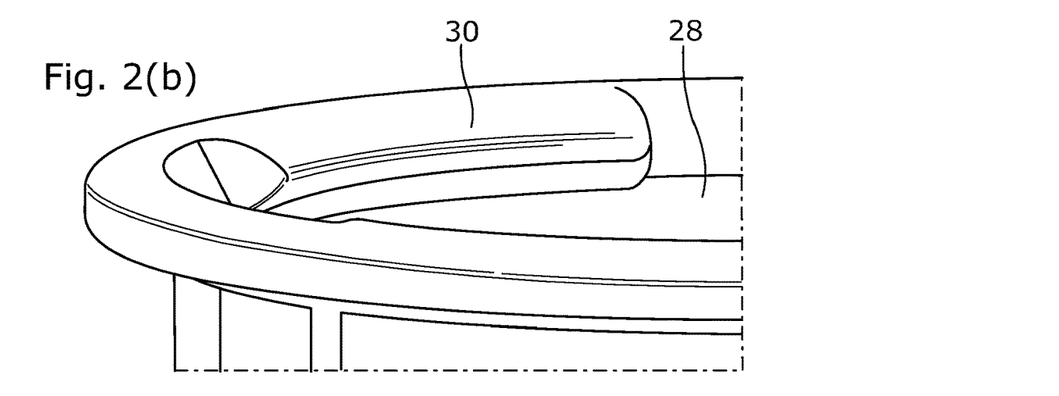

Referring now to the embodiment of FIGS. 2(a) and (b), here the storage compartment 16 is shown with a cylindrical socket 26 which includes splines 20 adapted to cooperate with the splines 22 on the needle hub 12, and a needle passage 24 extending away from the socket 26. This geometry is substantially reproduced in the removal compartment. At the outer periphery of the removal socket 28 (only) there are provided a number of inwardly extending arcuate abutment ribs 30 which define an aperture which is slightly smaller in diameter than the needle hub so that, when the needle hub 12 is pushed in, it snaps past the arcuate abutment ribs 30 to be retained thereby in the socket. When in this position, the needle hub 12 is held fully within the socket with no part thereof projecting beyond open end face of the socket. Conveniently, as shown in FIGS. 2(a) and (b), the arcuate abutment ribs 30 may be formed of a different plastics material to that from which the remainder of the device is moulded, having a contrasting collar and/or different material properties. For example, the device may be moulded in a two-shot moulding process with the arcuate abutment ribs 30 and a suitable graphic symbol 32 such as that of a padlock and/or an arrow labelling the storage compartment for ease of use. The plastics material making up the arcuate abutment ribs 30 may be designed to be more flexible than that of the remainder to facilitate the snap action.

Figure 3A:
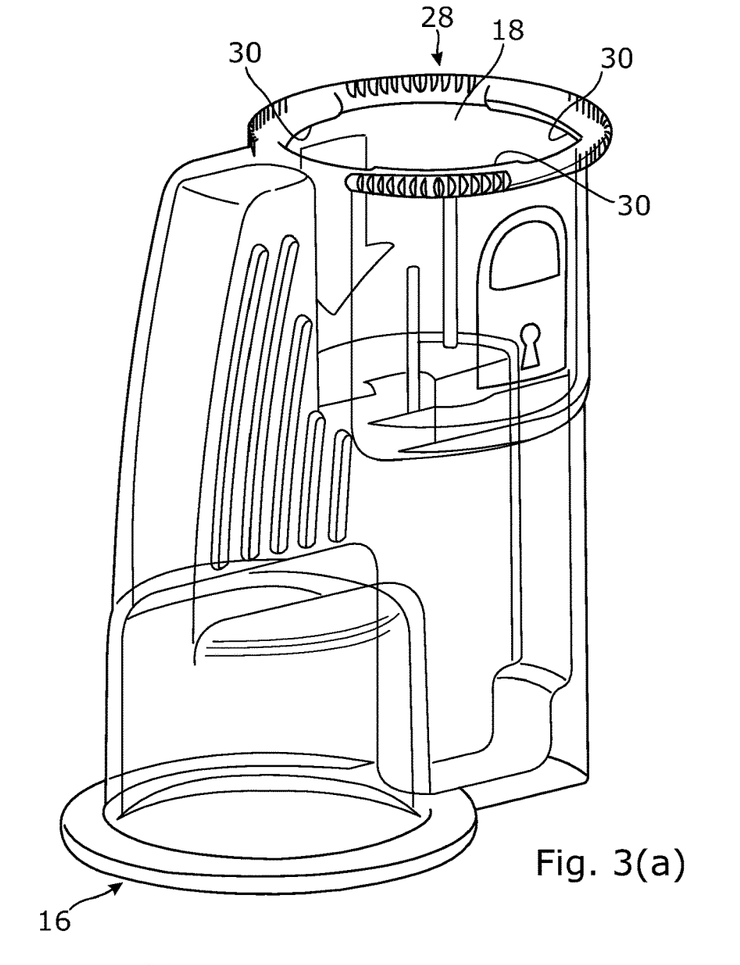
FIGS. 3(a) and (b) are side and detail views on a second embodiment of needle tip storage and removal device in accordance with this invention.
Figure 3B:
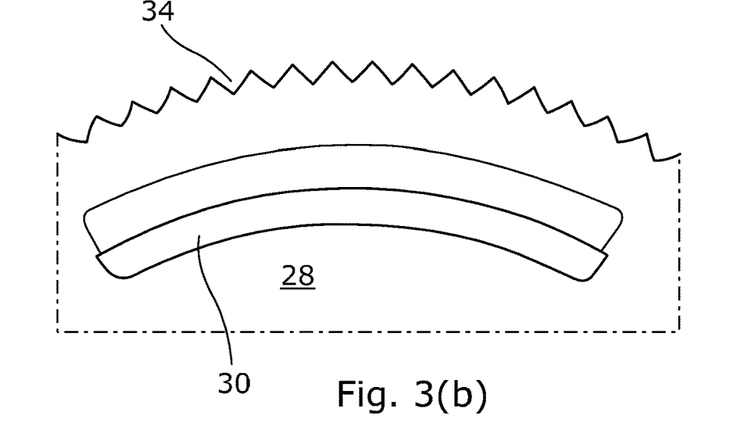

Referring now to the embodiment of FIGS. 3(a) and (b), here the device is provided with a toothed flange 34 around the periphery of the socket 28 in the removal compartment 18 to differentiate it from the storage compartment 16.

Figure 4A:
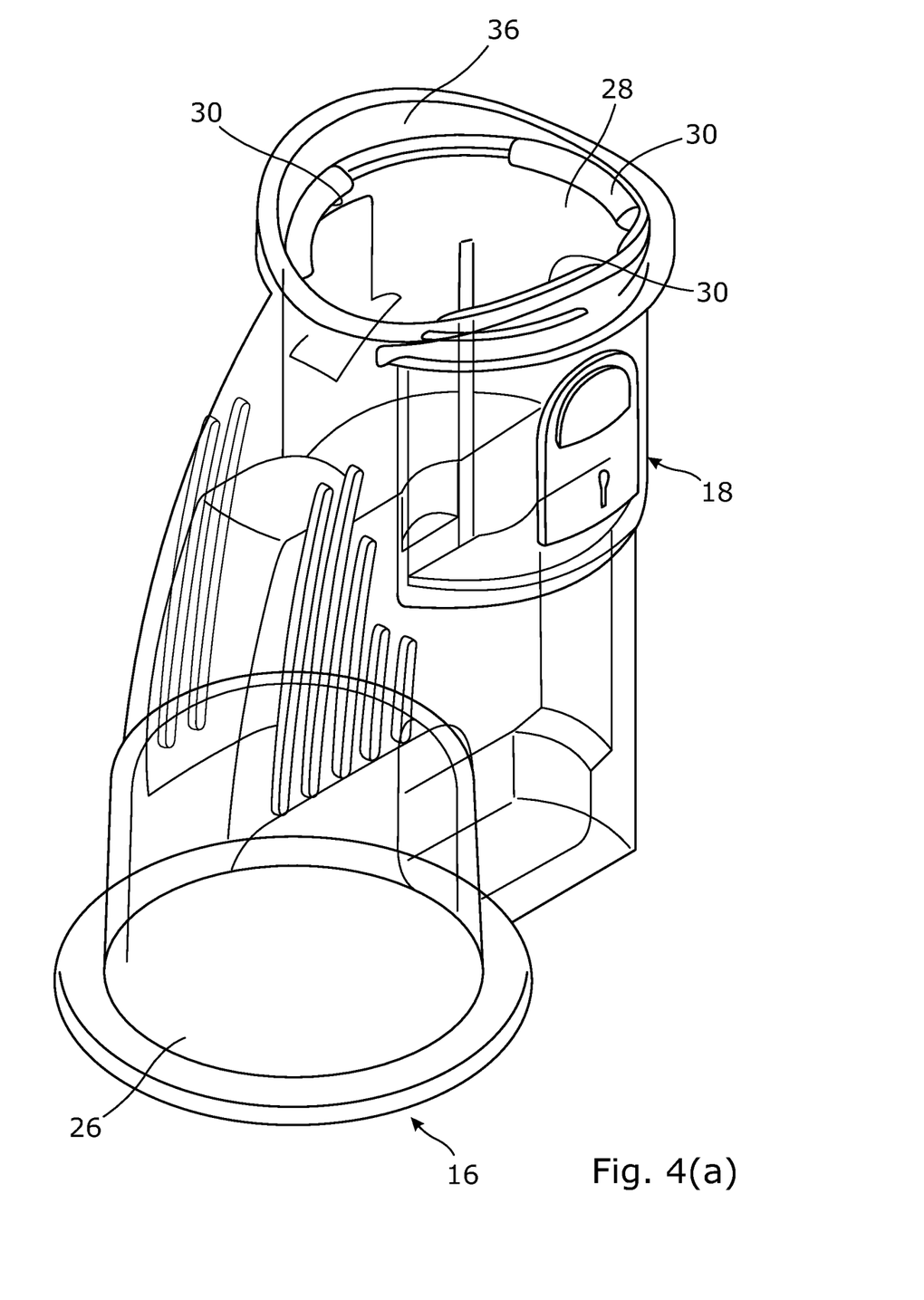
FIGS. 4(a), (b) and (c) are perspective, side and front views respectively of a third embodiment of needle tip storage and removal device in accordance with this invention.
Figure 4B:
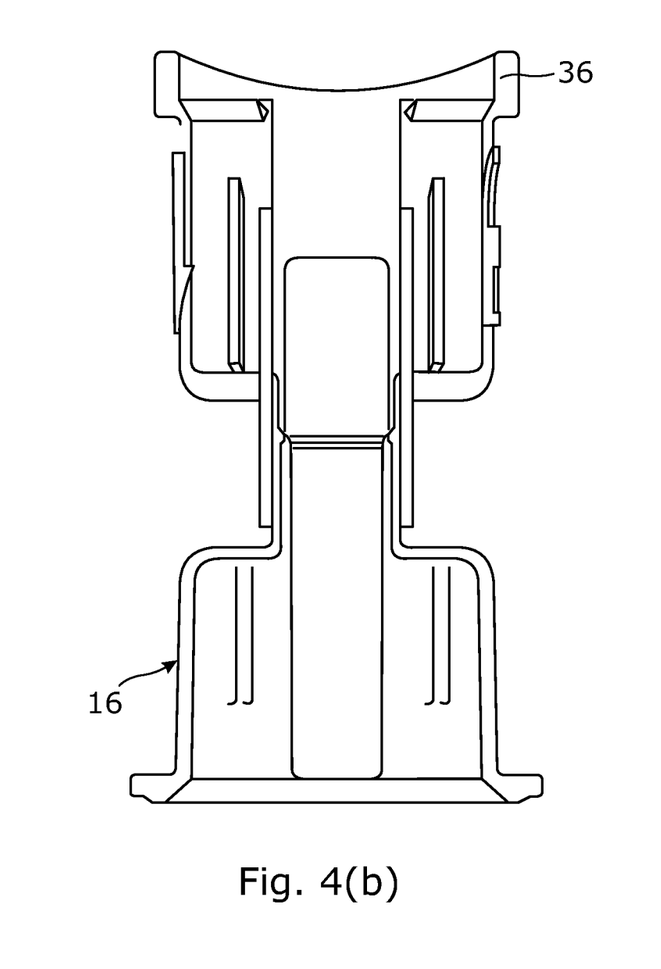
Figure 4C:
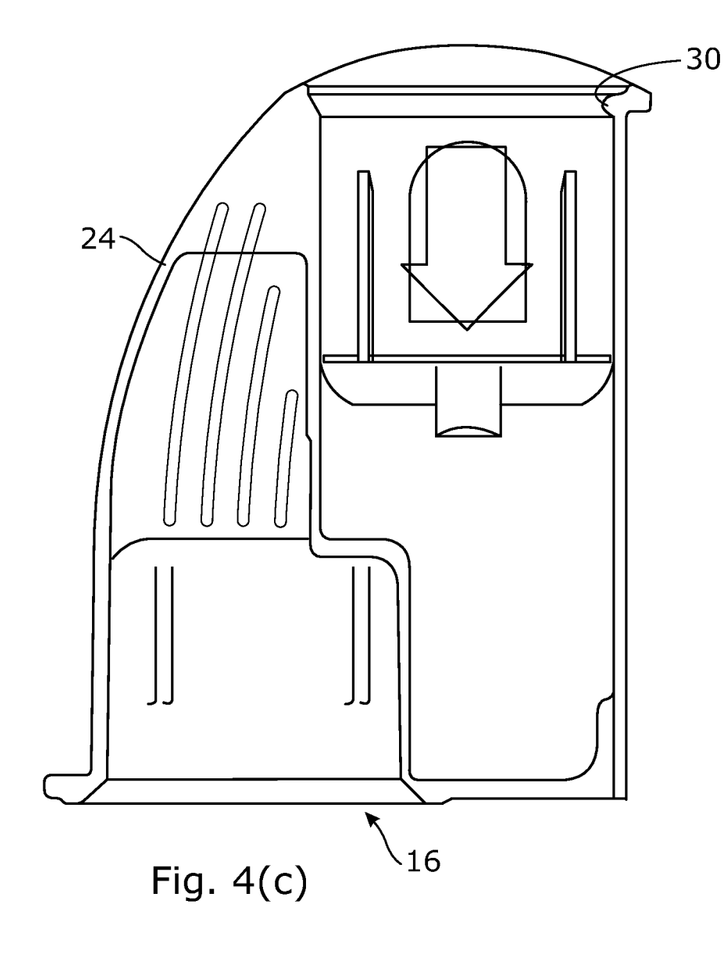
Figure 5A:
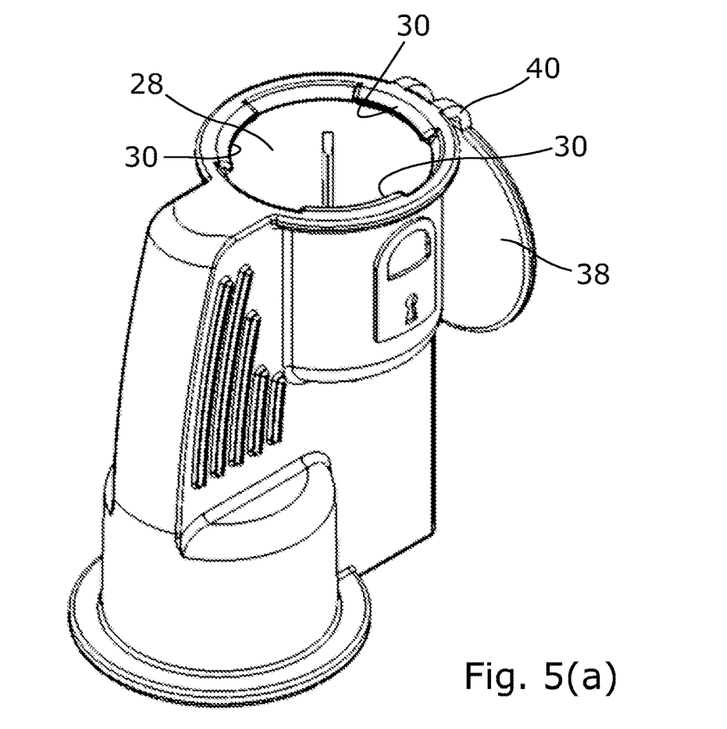
FIGS. 5(a) to (d) are views of a fourth embodiment of a needle tip storage and removal device in accordance with this invention.
Figure 5B:
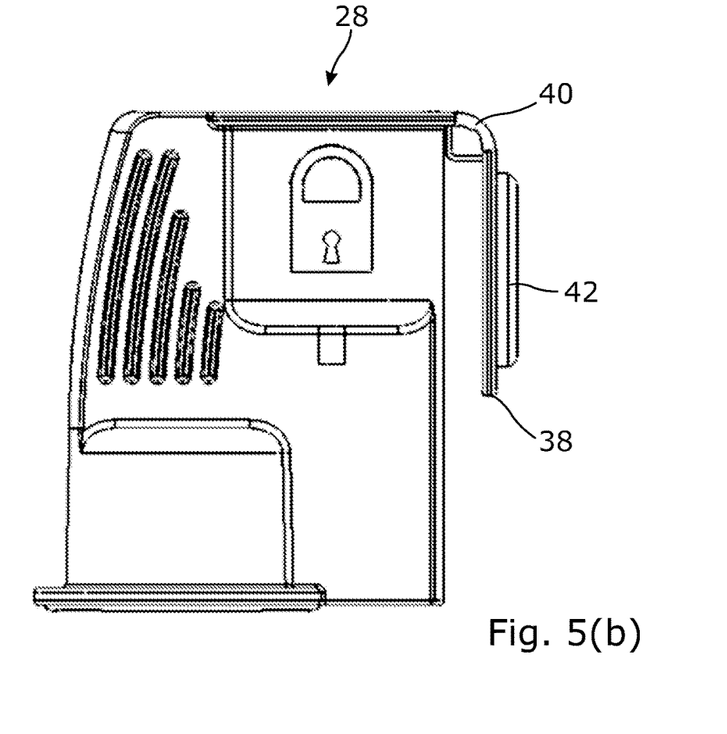
Figure 5C:
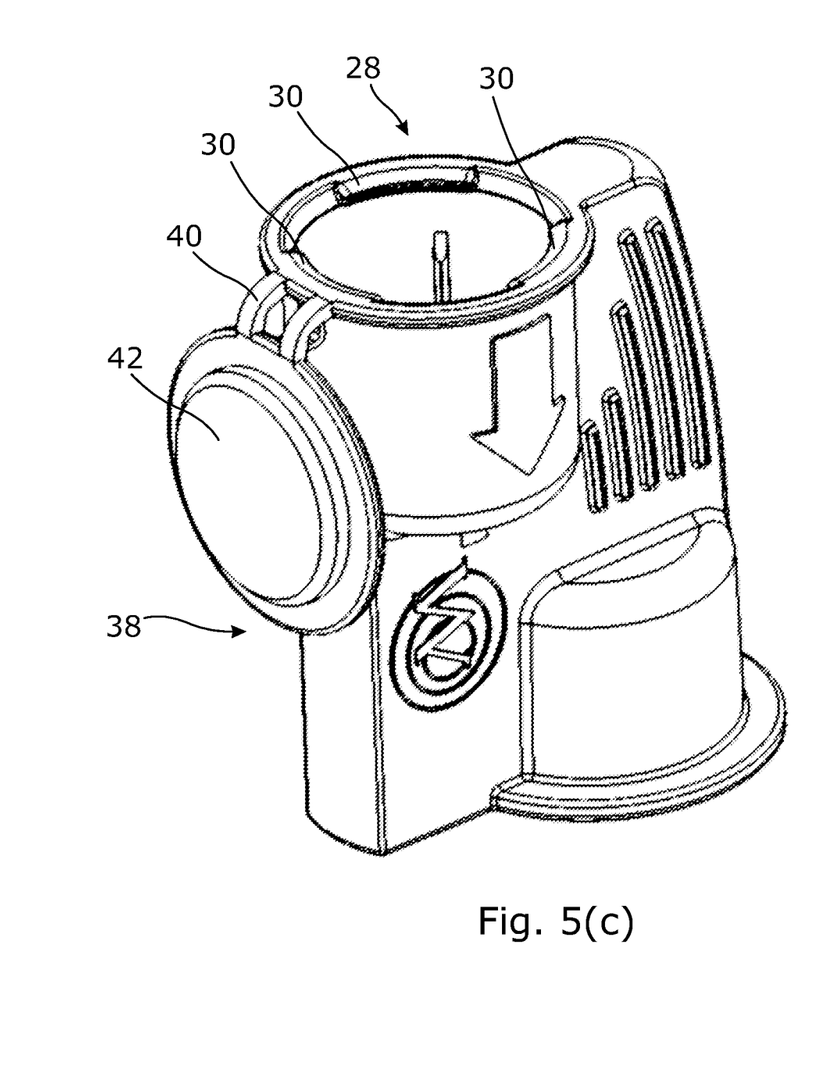
Figure 5D:
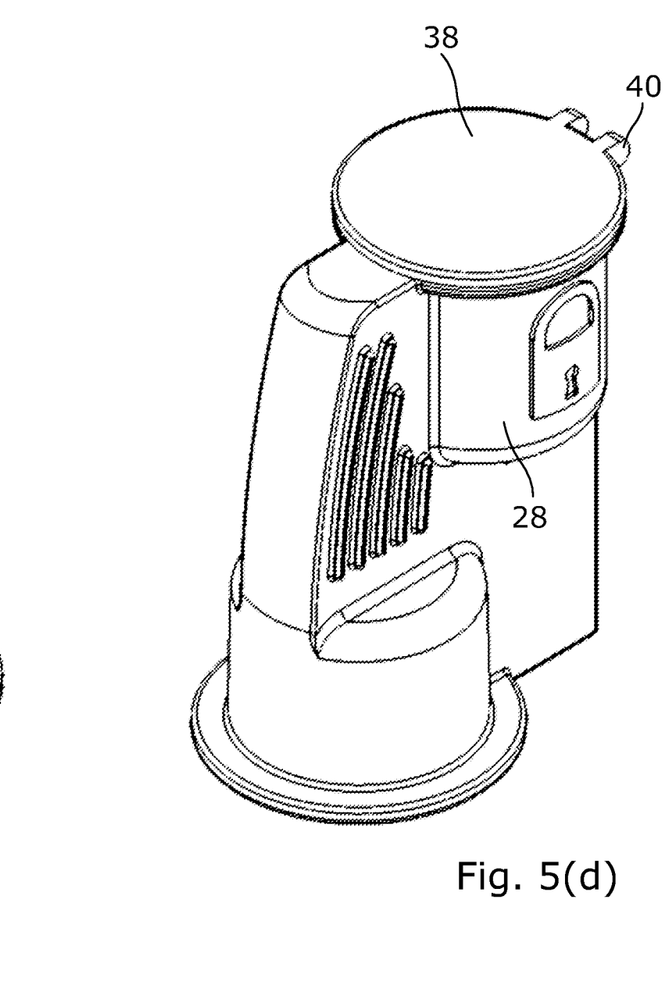
Figure 6A:
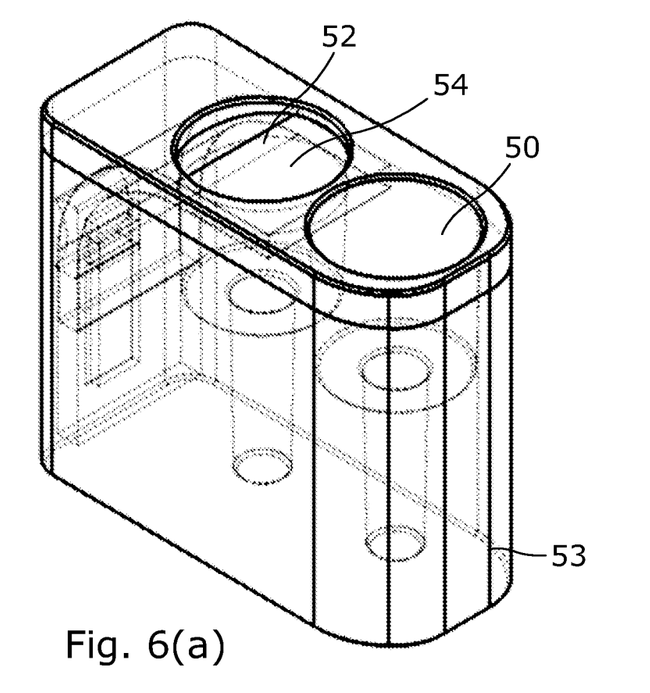
FIGS. 6(a) to (d) are views of a fifth embodiment of a needle tip and storage and removal device in accordance with this invention in both the open and closed positions.
Figure 6B:
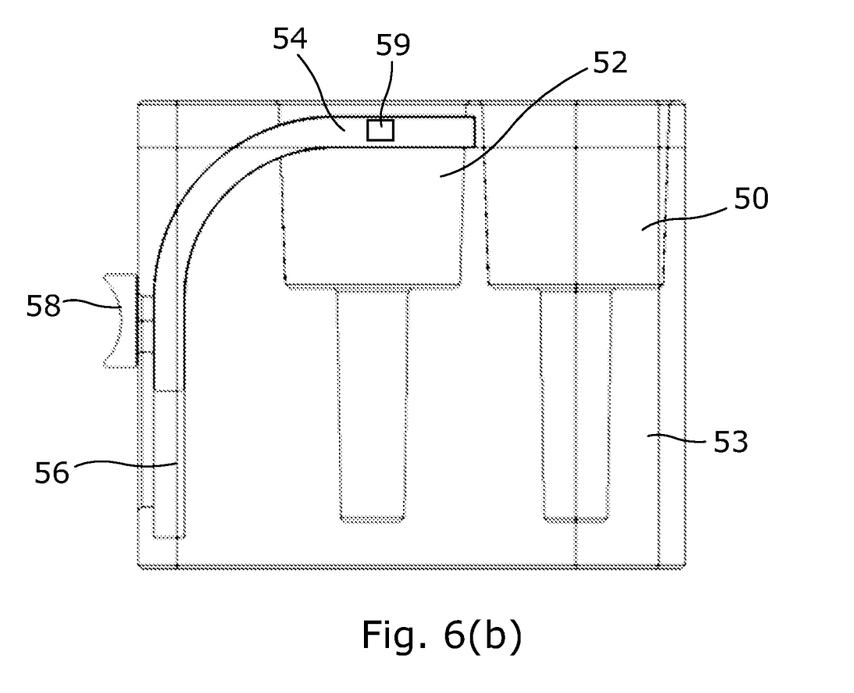
Figure 6C:
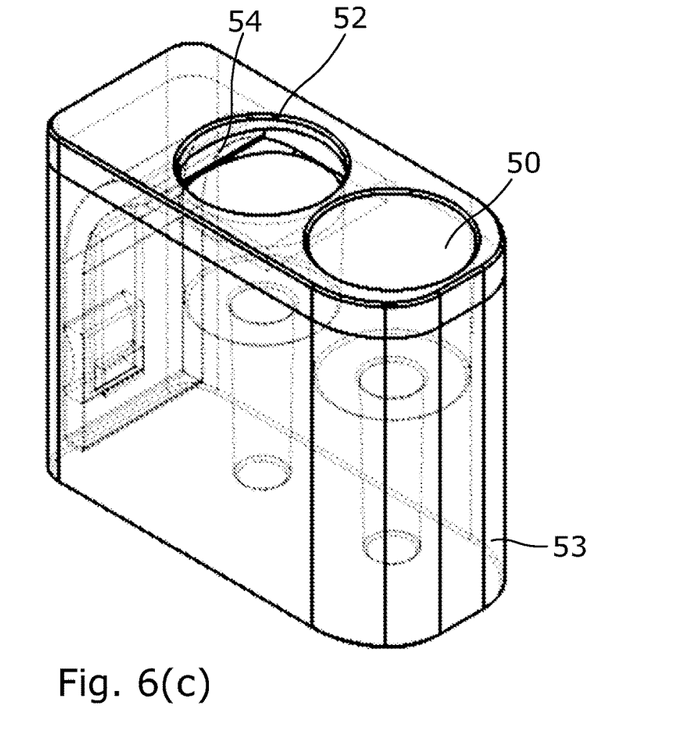
Figure 6D:
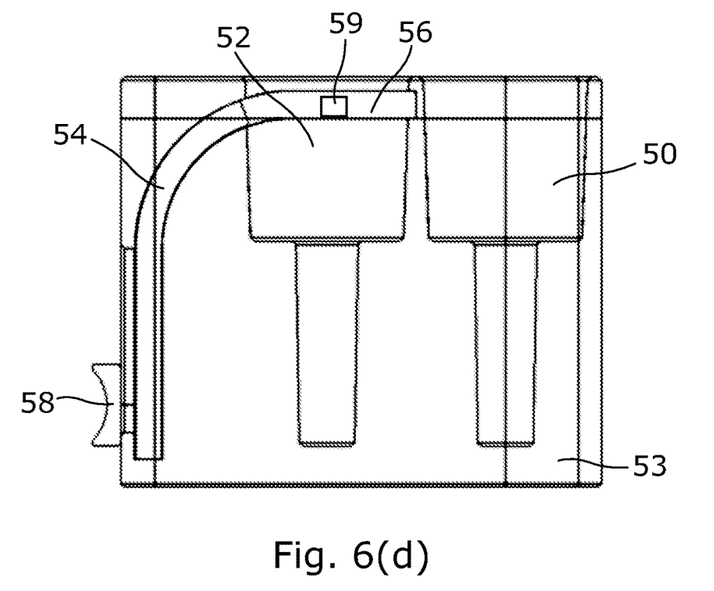

Referring now to the embodiment of FIGS. 4(a) to (c), here an undulating wall portion 36 extends around the socket 28 in the storage compartment, again to allow the user to distinguish it from the removal compartment. The undulating wall ensures that there is only one stable vertical orientation for the device, i.e. that as the device is viewed in FIG. 4, with the storage compartment facing downwards. As best seen in FIG. 4(c), in this configuration the base is flat and coplanar, whereas the opposite end is curved.

Figure 1:
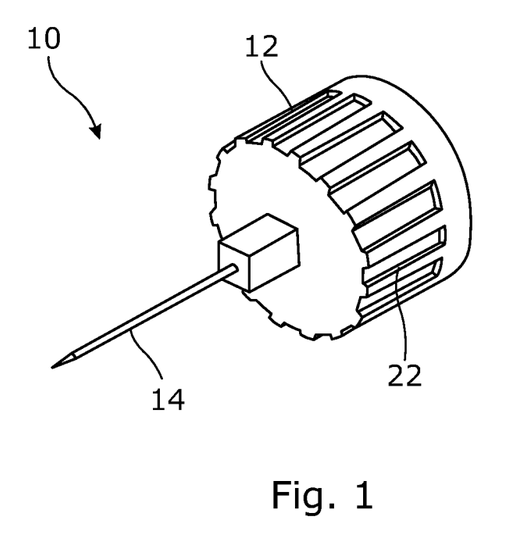
FIG. 1 is a view of a typical needle tip with which the various embodiments below are intended to be used.

Referring now to FIGS. 5(a) to (d), in this arrangement, the embodiment of FIG. 1 is supplemented by the provision of a cap 38 which is hinged to a wall portion of the device adjacent the socket in the storage compartment by a live hinge 40. The cap has a plug 42 that cooperates with the arcuate abutment ribs 30 so that the cap 38 may be snapped shut to prevent access to the used needle tip 10 once it has been inserted into the storage compartment and snapped past the arcuate abutment ribs 30.

Referring now to the embodiment of FIGS. 6(*a*) to (*d*), in this arrangement the splined storage compartment 50 and the removal compartment 52 are arranged side by side in the same orientation in a housing 53 which slideably mounts a flexible cover element 54. The cover element runs in a curved, L-shaped track 56 within the housing, with a thumb pad 58 extending through a slot in the housing so that the flexible cover can be slid from the open position shown in FIGS. 6(*c*) and (*d*) and the closed position shown in FIGS. 6(*a*) and (*b*) by sliding the thumb pad 58. If required, the device could be supplied with the shutter in the open position with a non-return catch indicated generally at 59 being provided between the shutter and the housing to prevent reopening of the storage container once the shutter has been closed.

Figure 7A:
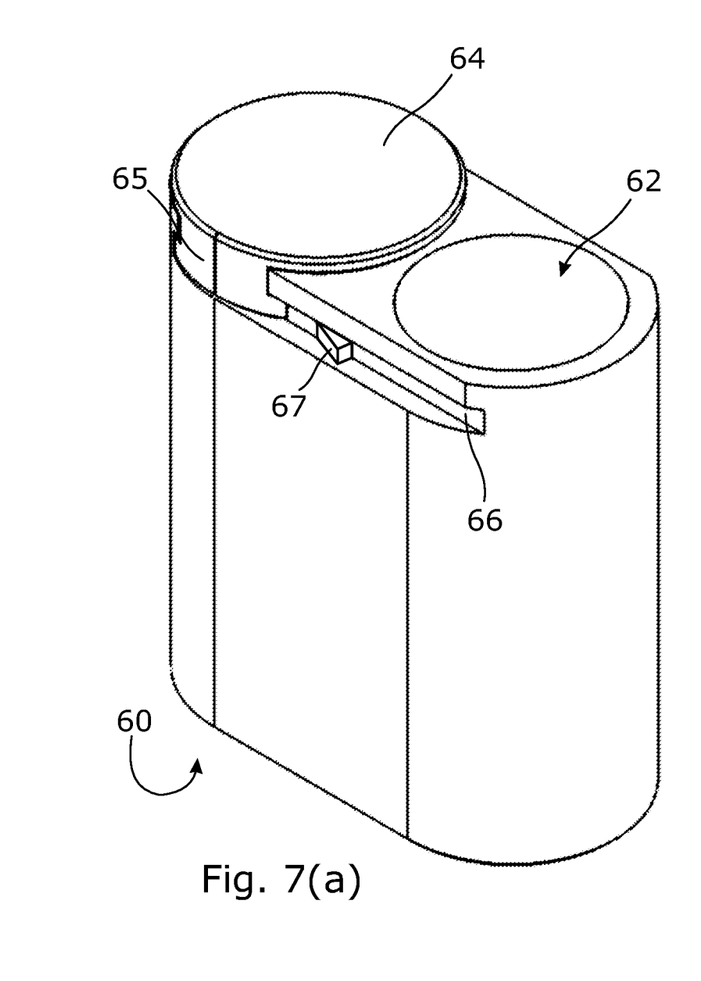
FIGS. 7(a) and 7(b) are side views of a sixth embodiment of a needle tip storage and removal device in accordance with this invention when in the open and closed positions respectively.
Figure 7B:
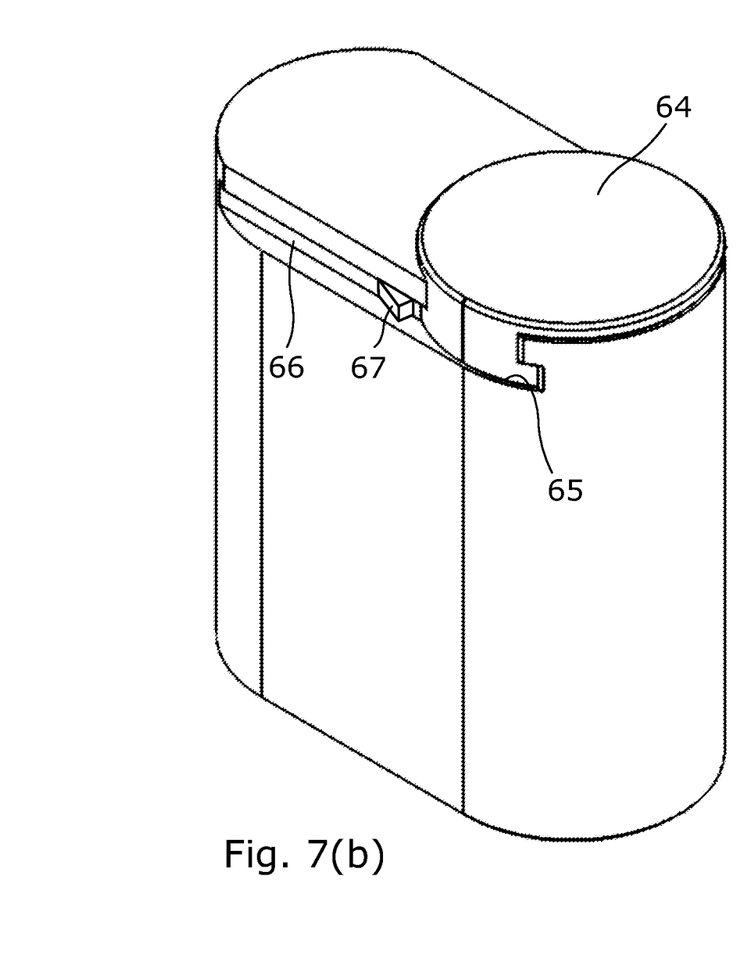
Figure 8A:
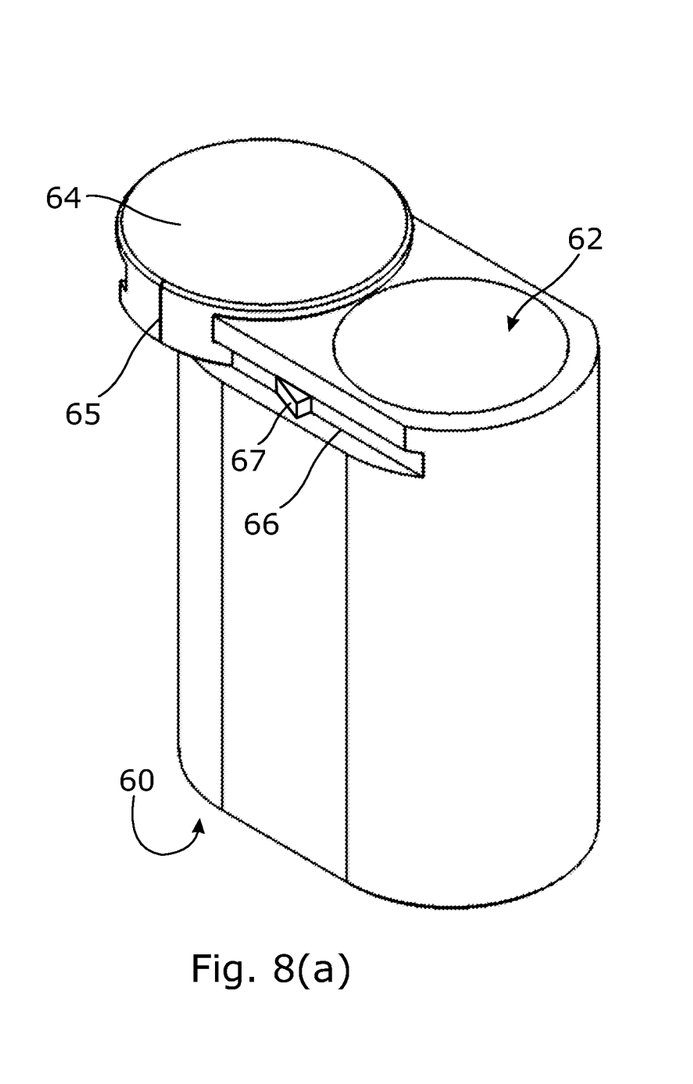
FIGS. 8(a) and (b) are side views of a seventh embodiment of a needle tip storage and removal device in accordance with this invention when in the open and closed positions respectively, and FIGS. 9(a) and (b) and 10(a) and (b) are comparative views showing alternative configurations of a needle tip and storage removal device in accordance with this invention.
Figure 8B:
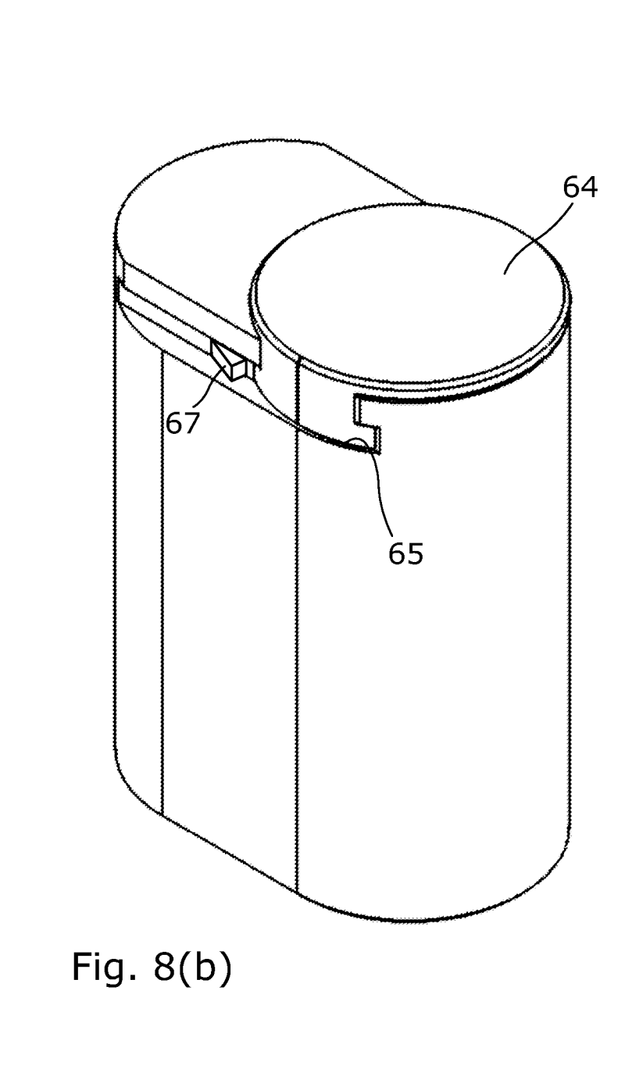

Referring now to the embodiments of FIGS. 7 and 8, in these arrangements the storage and removal compartments 60, 62 are oppositely directed as in the embodiments of FIGS. 1 to 5. In the views as shown, a disk shaped cover 64 has clips 65 which clip in opposite tracks 66 in the exterior of the housing (only one of which is shown) so that the cover can be slid between an open position (FIG. 7(*a*), FIG. 8(*a*)) and a closed position (FIG. 7(*b*), FIG. 8(*b*)). As previously, a non-return arrangement 67 may be provided so that, when the cover 64 is closed over the storage compartment 62, it cannot be reopened.

Figure 9A:
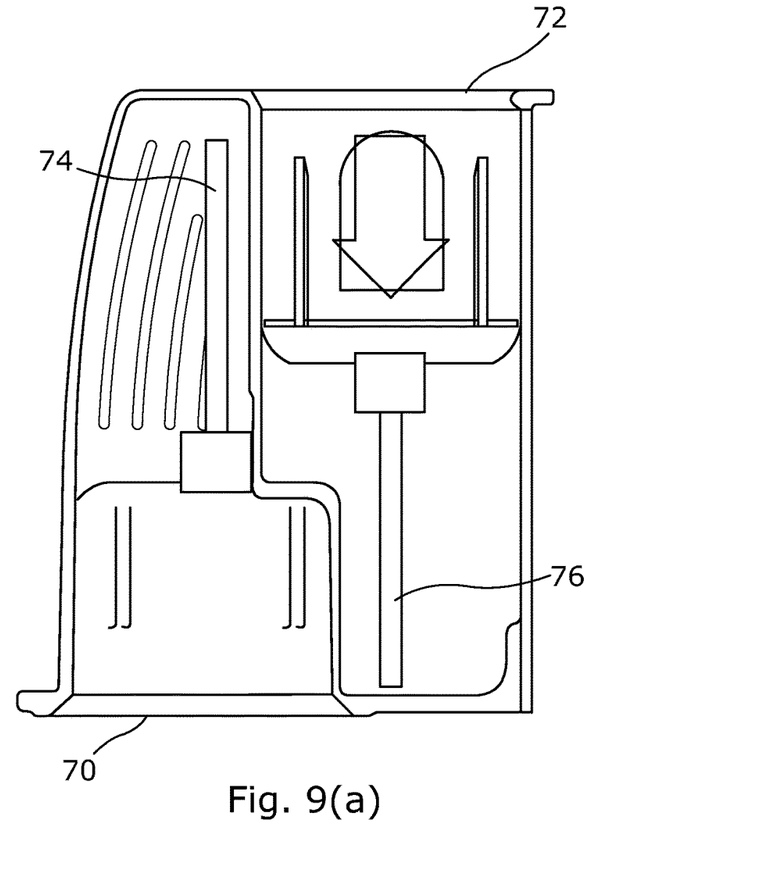
Figure 9B:
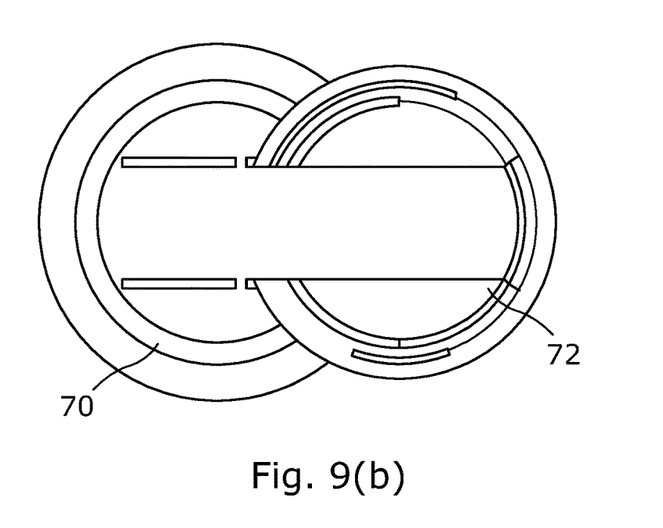
Figure 10A:
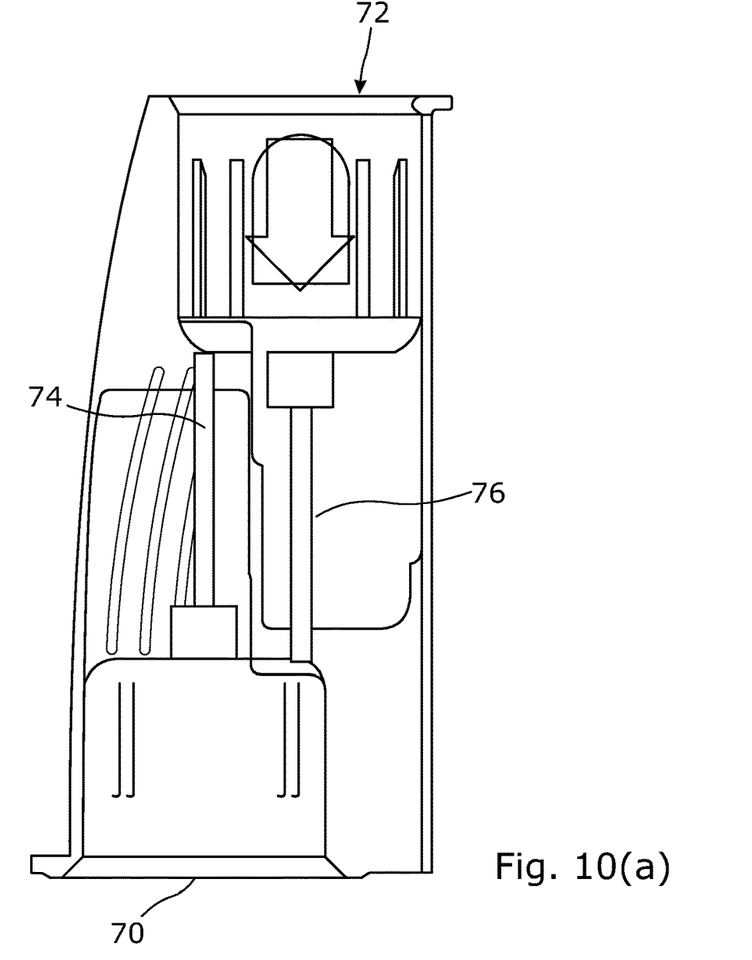
Figure 10B:
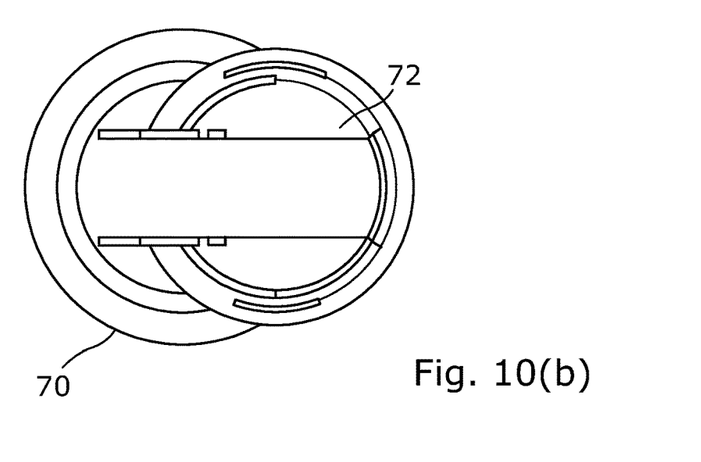

Referring now to FIGS. 9 and 10, these illustrate two different stacking configurations for the storage and removal compartments 70, 72 when they are oppositely directed. FIG. 9 shows a first stacking arrangement which provides a short and squat arrangement. Here the forward part of the needle passages 74, 76 of each compartment extend and lie alongside the socket portion of the other container with the needle passages staggered longitudinally. In the arrangement of FIG. 10, the needle passages 74, 76 lie alongside each other and are parallel and inversely aligned, which means that the width of the device can be reduced, but at the expense of increased height. In this configuration, the forward end of the passage of the removal compartment lies alongside the cylindrical socket of the storage compartment, and at least a portion of the distal end of the forward end of removal compartment terminates upon a shoulder of the cylindrical socket of the storage compartment. This provides a device of reduced transverse cross-section which facilitates posting of the device through an inlet opening of a sharps bin.

The invention claimed is:

1. A needle tip storage and removal device comprising a storage compartment for receiving in use an unused needle tip of a given drive configuration comprising a cylindrical skirt, the storage compartment comprising a cylindrical socket and, adjacent said storage compartment, a removal compartment for receiving in use a used needle tip of said given configuration, wherein the removal compartment includes a cylindrical socket and snap engagement means adjacent an outer periphery of the cylindrical socket of the removal compartment for cooperating with said skirt to retain a used needle tip when pressed into said cylindrical socket of the removal compartment in use, wherein each of the storage and removal compartments comprises a respective wall defining the respective cylindrical socket for a hub of the needle tip, and extending away therefrom an elongate narrower passage to receive a needle of the needle tip, with the storage compartment and the removal compartment being oppositely directed;

wherein the passages lie parallel and alongside each other; and wherein the wall of the cylindrical socket of the storage compartment defines a first longitudinal axis, and a second longitudinal axis is defined by a vertical axis of one of the passages and is parallel to the first longitudinal axis, wherein the second longitudinal axis passes through the cylindrical socket of both the storage and removal compartments and is centrally aligned within the one of the passages.

2. The needle tip storage and removal device according to claim 1, wherein the snap engagement means comprises spaced arcuate rib portions directed radially inwardly around the outer periphery of the socket of the removal compartment.

3. The needle tip storage and removal device according to claim 1, wherein the removal compartment is formed of moulded plastics material, and the snap engagement means are formed of a different plastics material.

4. The needle tip storage and removal device according to claim 1, wherein the socket of the removal compartment is designed so that in use a used needle tip may be fully retained in said socket by said snap engagement means, without protruding beyond the socket.

5. The needle tip storage and removal device according to claim 1, wherein the passage of each of the storage and the removal compartments defines a forward end, the forward end of the passage of the storage compartment lies alongside the cylindrical socket of the removal compartment, with the passages staggered.

* * * * *